(12) United States Patent
Aghion

(10) Patent No.: US 6,517,540 B2
(45) Date of Patent: Feb. 11, 2003

(54) UNIVERSAL DEVICE FOR THE PROTECTION OF SURGICAL PINS

(76) Inventor: Michael Aghion, 44 rue de l'Alma, Courbevoie 92400 (FR)

(*) Notice: Subject to any disclaimer, the term of this patent is extended or adjusted under 35 U.S.C. 154(b) by 0 days.

(21) Appl. No.: 09/901,658

(22) Filed: Jul. 11, 2001

(65) Prior Publication Data
US 2002/0007185 A1 Jan. 17, 2002

(30) Foreign Application Priority Data
Jul. 11, 2000 (FR) .......................................... 00 09024

(51) Int. Cl.$^7$ ................................................. A61F 5/04
(52) U.S. Cl. ......................................................... 606/53
(58) Field of Search ............................. 606/66, 53, 54, 606/72, 86; 411/372.5, 372.6, 373, 374, 375, 396, 397, 923, 480

(56) References Cited

U.S. PATENT DOCUMENTS

| | | | | |
|---|---|---|---|---|
| 3,485,134 A | * | 12/1969 | Ott | 411/372.5 |
| 4,976,712 A | * | 12/1990 | VanderSlik | 606/59 |
| 5,300,072 A | * | 4/1994 | Aghion | 606/59 |
| 5,300,075 A | * | 4/1994 | Gordon | 606/72 |
| 5,752,952 A | * | 5/1998 | Adamson | 606/54 |
| 5,860,779 A | * | 1/1999 | Toosky et al. | 411/432 |
| 6,086,972 A | * | 7/2000 | Rayburn et al. | 428/40.1 |

* cited by examiner

Primary Examiner—Eduardo C. Robert
(74) Attorney, Agent, or Firm—Young & Thompson

(57) ABSTRACT

A universal external device for the protection of the emerging portion of a surgical pin (6) of any diameter used, includes a protective element (1) provided with an axial cylindrical through bore (2) in which is disposed a resiliently deformable insert (5) adapted to receive the projecting end of the pin (6), as well as a locking screw (4) disposed in a tapped hole (3) which opens into said bore (2). The resiliently deformable insert (5) is cylindrical, of a shape and size adapted to those of the axial cylindrical bore (2) which has a distal abutment (2a), the insert (5), under the force of the pressure of the screw (4), deforming and trapping the pin (6) disposed in the insert (5) to prevent any risk of becoming embedded.

8 Claims, 2 Drawing Sheets

UNIVERSAL DEVICE FOR THE PROTECTION OF SURGICAL PINS

BACKGROUND OF THE INVENTION

The present invention relates to a universal device for external securement, adapted to protect the projecting end of the surgical pins currently used in general traumatology, in particular in the reduction of osseus fractures of the hand and foot.

The pins now used in traumatology of the hand, have incremental diameters from 0.7 to 2 mm. There exists for the protection of the projecting portion of these pins, an external spherical device pierced diametrically, adapted to receive pins of similar diameters. This device is also provided with a tapping disposed in the equatorial plane, in which a headless screw under the action of a screwdriver applies a point pressure on the pin inserted in the device, such that the protective device is immobilized in rotation and in translation on the pin, preventing it from migrating into the wound. There has been proposed by EP 0 527 204, a spherical universal protective device, provided with a bore for a pin, and a locking screw disposed in a hole which opens into said bore in which is disclosed an insert in the form of a resiliently deformable crescent, which under the locking force of said screw, locks the pin by circumconvolution of the two edges of the insert.

There is thus obtained a protection device which simply matches all of the diameters of the pins with the help of a single bore. The production of such a device is costly, its assembly complex and its use with a pin of a diameter of 2 mm can drive the insert out of the bore diametrically.

So as to overcome these drawbacks, the present invention has for its object to provide a new universal device for the protection of surgical pins, simple in structure and easy to use.

SUMMARY OF THE INVENTION

To this end, the invention has for its object an external universal device for the protection of the emergent portion of a surgical pin of any diameter used, of the type comprising a protection element provided with an axial cylindrical through bore in which is disposed a resiliently deformable insert adapted to receive the projecting end of the pin, as well as a locking pin disposed in a tapped hole which opens into said bore, characterized in that the resiliently deformable insert is cylindrical, of a shape and dimension adapted to that of the axial cylindrical bore, which has a distal abutment, the insert, under the influence of the pressure of the screw, deforming and trapping the pin disposed in said insert to prevent any risk of becoming buried.

According to a first embodiment, the axial cylindrical bore is partially tapped and the resiliently deformable insert has a complementary screw thread on its external surface so as to be able to be screwed into said bore. Thus, preferably, the insert is designed according to the dimensions permitting it to be screwed into the axial bore of the protective element.

According to a second embodiment, the resiliently deformable insert is disposed and cemented into the axial cylindrical bore.

According to a third embodiment, the resiliently deformable insert is set in the axial cylindrical bore.

The universal protective device according to the invention, thus permits precise adaptation to all diameters of pin currently used in the reduction of osseus fractures of the hand or foot with a single axial bore, without risk that the insert will be ejected from the bore by use of a pin of a large diameter such as 2 mm.

The resilient property of the insert permits it to deform during screwing of the screw to trap the pin, then to recover its initial shape during unlocking of the screw, which has the effect of freeing the pin.

Such a device according to the invention, can be adapted to surgical pins whose diameter is comprised between 0.7 and 2 mm. However, a device quite identical but designed according to suitable dimensional sizes, can be adapted to pin diameters from 2 to 6 mm and so on.

The universal protective device comprises a protection element which can be of spherical shape, but which could also have a cubic, cylindrical, parallelepipedal, oblong, pyramidal shape or even any other suitable shape.

BRIEF DESCRIPTION OF THE DRAWINGS

There will be described in what follows, in greater detail, an example of the invention with reference to the accompanying drawings, in which.

DETAILED DESCRIPTION OF THE PREFERRED EMBODIMENTS

Figure 1:
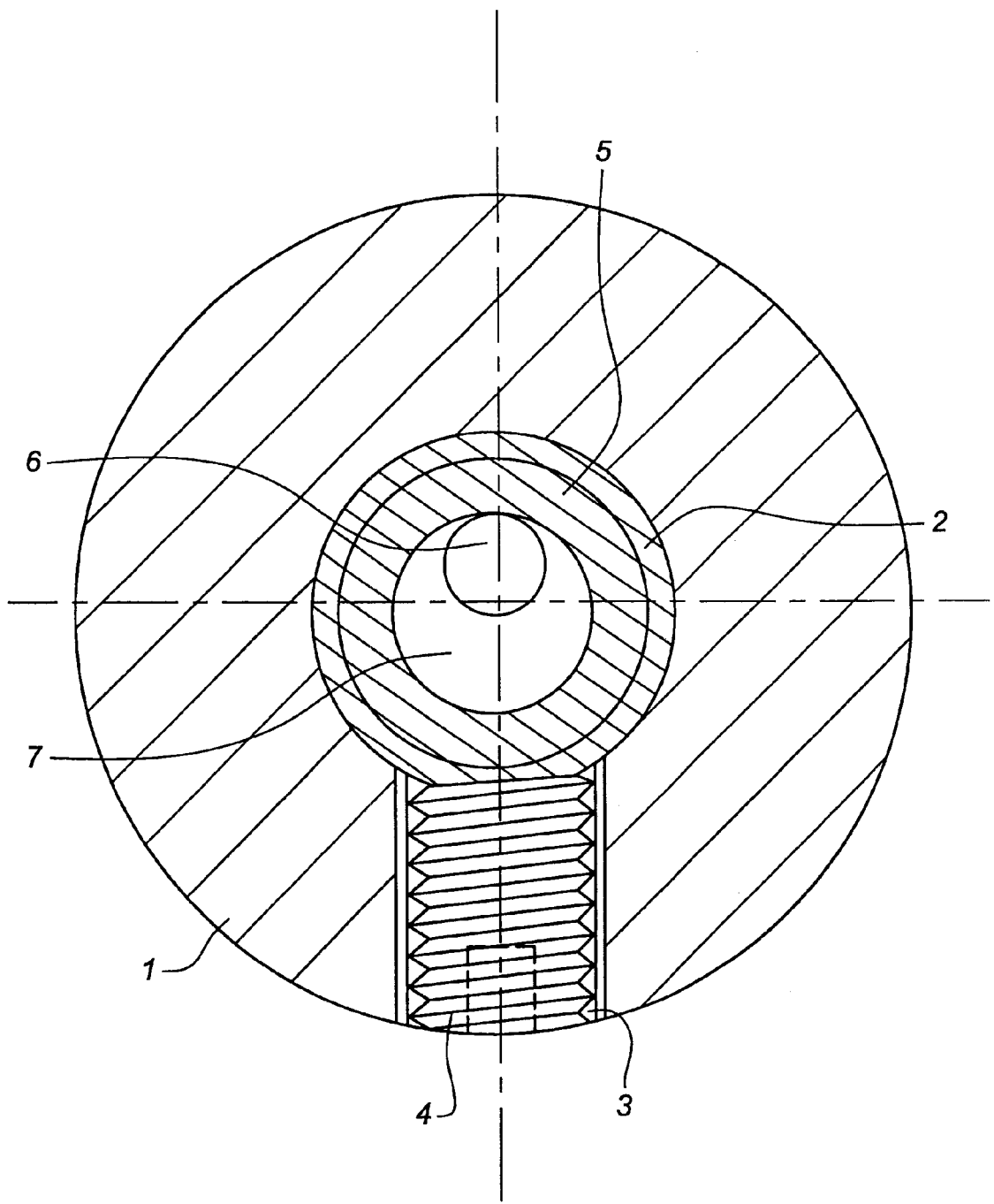
FIG. 1 is a transverse cross-sectional view of the universal protective device for pins.
Figure 2:
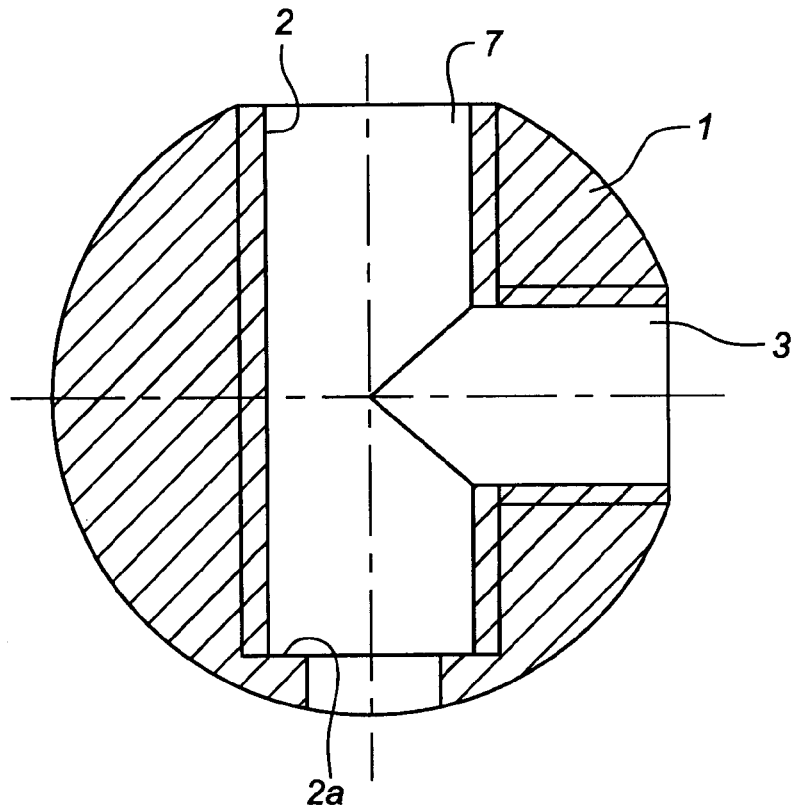
FIG. 2 is a cross-sectional view of the universal protective device for pins, shown in FIG. 1, and FIGS. 3a and 3b show respectively a perspective view and a cross-sectional view of the insert of the device of FIG. 1.
Figure 3A:
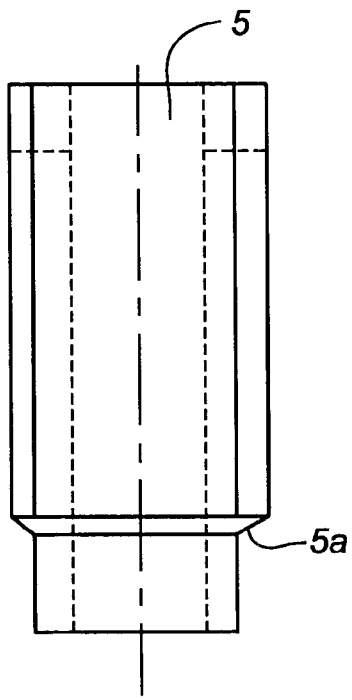
Figure 3B:
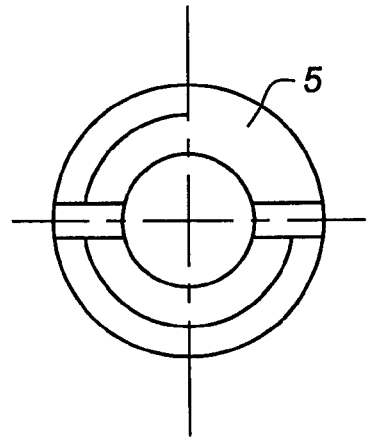

The universal protective device for pins according to the invention, comprises a protective sphere 1 provided with a cylindrical axial bore 2 containing a distal abutment 2a.

A tapped hole 3 opens into said bore 2 and receives a locking screw 4.

The axial cylindrical bore 2 is partially tapped and receives a hollow cylindrical insert 5 defining a through hole 7 in which can be disposed a pin 6, of a shape and size adapted to those of the axial bore 2 and made of a resiliently deformable material. This resiliently deformable insert is screw threaded on its external surface so as to be adapted to be screwed into said bore 2 and can have a shoulder 5a suitable to come into engagement against the distal abutment 2a which limits its introduction into the bore 2.

When the screw 4 is screwed in, the insert 5 deforms, and fixes itself securely to the pin 6 which is engaged in the hole 7 defined by the insert 5, in the manner of the jaws of a vise to as to trap the pin 6. When the screw 4 is unscrewed, the insert 5, because of the resilience of its material, regains its original shape and frees the pin 6.

What is claimed is:

1. A universal external device for protecting an emergent portion of a surgical pin, comprising:
   a protective element having an axial cylindrical through bore and a tapped hole intersecting said bore;
   a resiliently deformable hollow cylindrical insert disposed in said bore for receiving an emergent portion of a surgical pin, the insert having a continuous wall surrounding a through hole; and
   a locking screw in said tapped hole for deforming said cylindrical insert.

2. The device according to claim 1, wherein said bore further comprises a distal abutment and said cylindrical insert further comprises a shoulder, said shoulder abutting said distal abutment.

3. The device according to claim 1, wherein said bore is at least partially tapped and said cylindrical insert further comprises a complimentary external screw thread surface for screwing said cylindrical insert into said bore.

4. The device according to claim 1, wherein said cylindrical insert is cemented in the bore.

5. The device according to claim 1, wherein said cylindrical insert is set in the bore.

6. The device according to claim 1, wherein said protective element is a sphere.

7. A universal external device for protecting an emergent portion of a surgical pin, comprising:

a protective element having an axial cylindrical through bore and a tapped hole intersecting said bore;

a resiliently deformable cylindrical insert disposed in said bore for receiving an emergent portion of a surgical pin, said cylindrical insert having a constant wall thickness throughout a circumference of said cylindrical insert; and a locking screw in said tapped hole for deforming said cylindrical insert to trap the pin between portions of an internal wall of the cylindrical insert.

8. A universal external device for protecting an emergent portion of a surgical pin, comprising:

a protective element having an axial cylindrical through bore and a tapped hole intersecting said bore;

a resiliently deformable cylindrical insert disposed in said bore; and a locking screw in said tapped hole for deforming said cylindrical insert, wherein deformation of said cylindrical insert is independent of a position of the locking screw.

* * * * *